(12) United States Patent
Tweardy

(10) Patent No.: US 8,459,264 B2
(45) Date of Patent: Jun. 11, 2013

(54) AIRWAY PAD

(75) Inventor: Lisa A. G. Tweardy, Thalwil (CH)

(73) Assignee: Ossur hf., Reykjavik (IS)

( * ) Notice: Subject to any disclaimer, the term of this patent is extended or adjusted under 35 U.S.C. 154(b) by 1102 days.

(21) Appl. No.: 10/638,979

(22) Filed: Aug. 12, 2003

(65) Prior Publication Data

US 2005/0034734 A1 Feb. 17, 2005

(51) Int. Cl.
*A61G 15/00* (2006.01)

(52) U.S. Cl.
USPC ......................................................... 128/845

(58) Field of Classification Search
USPC .............. 128/870, 846, 845; 5/655, 722, 723, 5/417, 420; 482/23, 142, 140
See application file for complete search history.

(56) References Cited

U.S. PATENT DOCUMENTS

| | | | | |
|---|---|---|---|---|
| 3,139,281 A | * | 6/1964 | Nicholson | 473/414 |
| 3,515,385 A | * | 6/1970 | Gunderson | 473/414 |
| 3,744,134 A | * | 7/1973 | Zima, Jr. | 33/768 |
| 4,811,489 A | * | 3/1989 | Walker | 33/759 |
| 4,823,469 A | | 4/1989 | Broselow | 33/760 |
| 4,985,952 A | * | 1/1991 | Edelson | 5/722 |
| 5,010,656 A | | 4/1991 | Broselow | |
| 5,048,136 A | * | 9/1991 | Popitz | 5/603 |
| 5,066,001 A | * | 11/1991 | Wilkinson | 482/52 |
| 5,099,530 A | | 3/1992 | Scott | |
| 5,156,409 A | * | 10/1992 | Barnes | 473/414 |
| 5,491,851 A | * | 2/1996 | Alonso | 5/722 |
| 5,669,077 A | * | 9/1997 | Stewart | 2/227 |
| 5,683,314 A | * | 11/1997 | Musso | 473/414 |
| 5,924,940 A | * | 7/1999 | Lucy, Jr. | 473/414 |

OTHER PUBLICATIONS

FunTastic Media. [Retrieved on Mar. 20, 2007]. Retrieved from the Internet: <URL: http://web.archive.org/web/20030215090650/www.funtasticmedia.com/baby_ruler.asp>.*
International Preliminary Examination Report for PCT Patent Application No. PCT/US2006/031321, dated Aug. 2, 2007.
International Search Report and Written Opinion dated Feb. 13, 2007 for PCT Patent Application No. PCT/US06/031321.
Article 34 Amendment and Arguments and Demand dated Jun. 12, 2007 for PCT Patent Application No. PCT/US06/031321.
Office Action dated Nov. 19, 2008 for U.S. Appl. No. 11/502,227.
Amendment and Response dated May 19, 2009 for U.S. Appl. No. 11/502,227.

* cited by examiner

*Primary Examiner* — Patricia Bianco
*Assistant Examiner* — Camtu Nguyen
(74) *Attorney, Agent, or Firm* — Schnader Harrison Segal & Lewis LLP (57) ABSTRACT

The present invention pertains to a method for aligning both the cervical spine and the airway of a child by elevating the spine of the child to allow some clearance for the head of the child to rest on a lower plane. In a preferred embodiment, the extent of maturity of the child is first estimated by measuring the length of the child or some portion of the child. Finally, a pad is provided which is height adjustable which can be used in the method of the present invention to elevate the spine of the child.

8 Claims, 11 Drawing Sheets

AIRWAY PAD

BACKGROUND

1. Field of the Invention

This invention relates to a therapeutic positioning apparatus, of particular use on infants and juveniles.

2. Description of Related Art

It is an unfortunate fact that people are often injured in accidents. The severity of injuries obtained in accidents can range from minor cuts and bruises to major physical trauma. It is another unfortunate fact that frequently those injured in accidents are juveniles. Oftentimes, the extent of an individual's injuries cannot be ascertained immediately at the scene of the accident. This is particularly difficult with infants because they are unable to communicate directly with emergency personnel. Additionally, in the case of any unconscious individual, the severity of injuries is difficult to ascertain, especially at an accident scene. Furthermore, even where individuals involved in an accident are conscious and communicative, it is difficult to ascertain the extent of an individual's injuries because those injured persons may not be fully aware of the extent of their own injuries.

Accordingly, in many cases, emergency personnel deem it prudent to immobilize the head and spinal column of the victim of an accident, in an abundance of caution. If there is an injury to the cervical spine and the head and torso of the victim are not immobilized, movement of the head and neck can result in damage to the spinal cord and permanent paralysis can result. Oftentimes one of the devices used to immobilize the head and neck of a victim is a backboard. Many times, an extrication collar is used in conjunction with a backboard. While backboards and other similar devices are effective for immobilization of the head and spine of an adult, they are less effective, and sometimes injurious, to infants and juveniles.

The anatomy of children is such that placement in a supine position on a backboard or other flat surface, such as an operating table or bed, will often orient the head and cervical spine in an anatomically flexed position, thus compromising spinal and airway alignment. It is critical to create or maintain an open airway for a victim. In the juvenile accident victim with an injured cervical spine, extending the head to open the airway can injure the neck and spinal cord, and may even result in paralysis. Accordingly, there is an acute need for a method to align both the airway and cervical spine of a juvenile victim of an accident and, indeed, any juvenile patient at risk of respiratory complications and/or requiring anatomical positioning for diagnostic testing or surgery.

SUMMARY OF THE INVENTION

The present invention pertains to a method for aligning both the cervical spine and the airway of a supine child by elevating the spine of the child relative to the occipital prominence. In a preferred embodiment, the child is first measured to estimate the degree of elevation necessary. In a further embodiment, the extent of maturity of the child is estimated by considering the length of the child or some portion of the child, or the child's weight or age. Finally, a pad is provided which is height adjustable which can be used in the method of the present invention to elevate the spine of the child.

The invention further includes a configurable apparatus wherein a parameter such as height correlates with indicia on the apparatus, so that when the apparatus is configured correctly the particular indicia appears in a certain location, indicating that the apparatus has been configured correctly. In a preferred embodiment, the apparatus is a support pad used to elevate the spine of a child in a supine position to align the spine and airway. The pad has measuring indicia to determine the size of the child. The pad is configured by folding it to achieve a thickness that produces the desired spine elevation. When the pad s folded to the correct configuration, indicia related to the measuring indicia appear in a particular location The invention also includes methods for aligning the cervical spine and airway of a child for configuring apparatus.

DETAILED DESCRIPTION OF THE INVENTION

It is widely documented in the medical literature, but not widely taken into account in devising medical devices and caring for pediatric patients, that juveniles are not simply small adults. The proportions of the juvenile body are different from the proportions of the adult human. Accordingly, in devising medical apparatuses for use with juveniles, these differences in proportions should be, but seldom are, taken into account. Unfortunately, many medical devices designed for use with adults, are simply shrunken in size for use with juveniles. In some cases this is appropriate, but in others the results can be disastrous. Such is the present case.

Figure 1A:
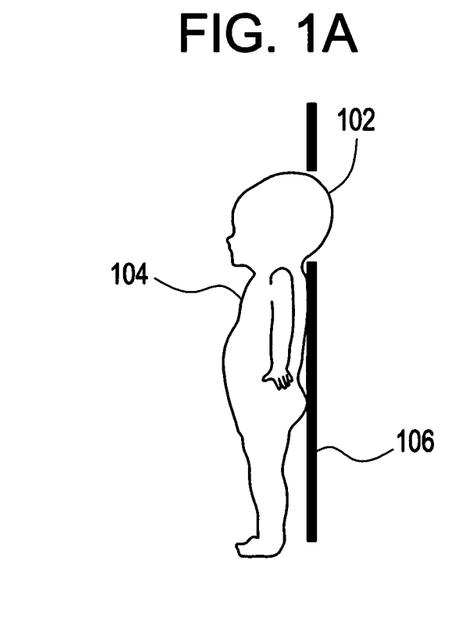
FIGS. 1A-B depict the head:body proportion of a juvenile and adult, respectively.
Figure 1B:
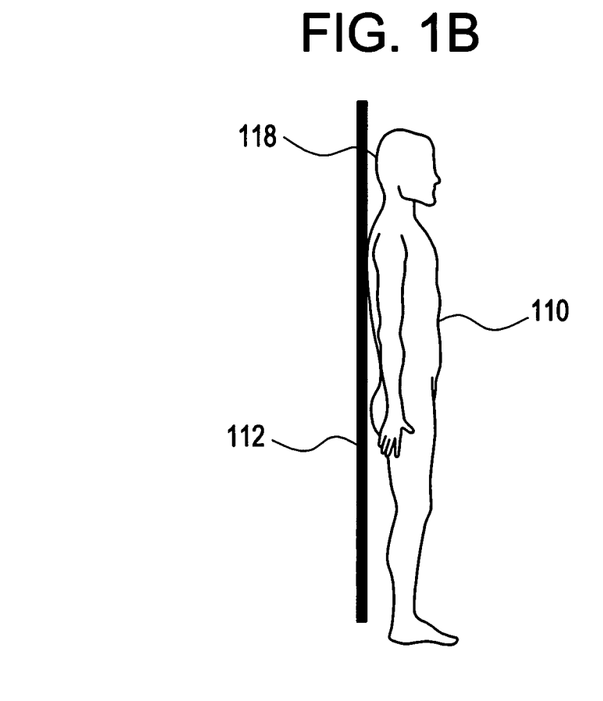
Figure 2A:
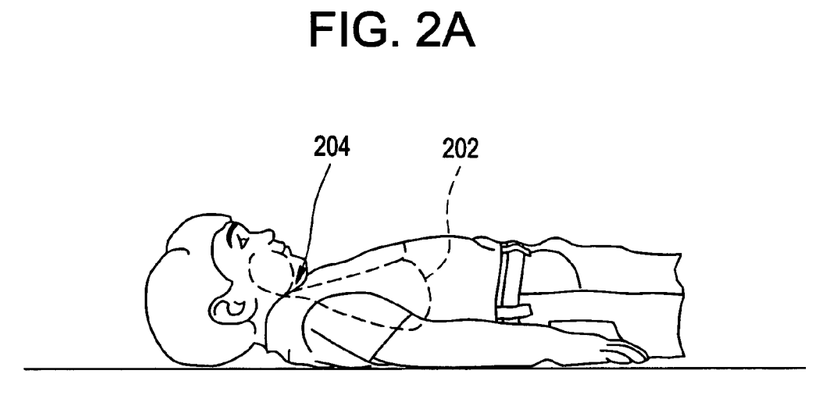
FIGS. 2A-C depict airways of a juvenile in a supine position.

In contrast to mature human beings, the head of a juvenile (especially ages 12 and under) is disproportionately large as compared to his or her body, as shown in FIGS. 1A-B. One consequence of this is that the occiput 102 of the child 104 extends beyond a plane 106 level with the back of the child. Accordingly, laying a child in a supine position on a flat surface pushes the head of the child forward causing a flexion of the neck. This can be seen from FIG. 2A where there is clear flexion of the neck of the child, and potential airway impairment. The broken lines 202 in FIG. 2A outline airways in the child's torso and head. It can be seen that airways are restricted in section 204 due to neck flexion. When a child is younger, the effect is more dramatic.

Figure 3A:
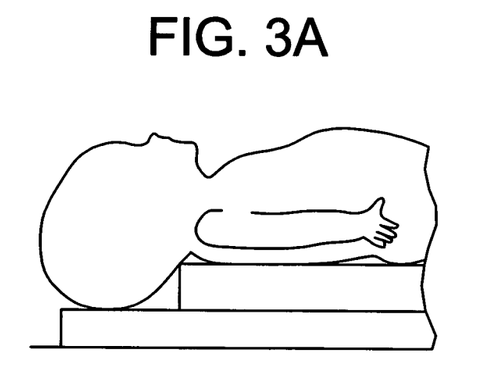
FIGS. 3A-B depict spinal alignment of a juvenile and adult, respectively.
Figure 3B:
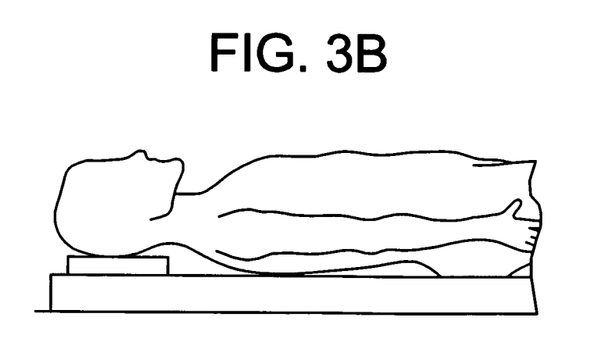

The proportionality of the child changes as the child grows. FIG. 1B shows how the occiput 118 of an adult 110 does not reach the plane 112 of the adult's back. Therefore, upon reaching maturity, in order to achieve alignment of the spine and airways when lying in a supine position on a flat surface, it is necessary to elevate the head of an adult, as shown in FIG. 3B. This method of alignment is not effective for a child, due to a child's head size with respect to its body size.

In trauma situations, it is most critical that the victim have an optimal airway to allow breathing. This may involve merely tilting the head so the victim can breathe on his or her own, or it may involve inserting a tracheal tube so that breathing may be assisted. In order to achieve this in a child lying supine on a flat surface, it is necessary to extend the head of the child and pull the jaw upward in order to align the airway and allow the child to breathe or allow proper insertion of an airway or tracheal tube. However, this maneuver causes extension of the cervical spine. In the case where a child has an injured or potentially injured cervical spine, this maneuver is contraindicated because it may cause paralysis. Nevertheless, emergency medical technicians are often trained to do just this in order to allow the child to breathe, which is clearly the most urgent and important consideration in keeping the child alive. However this may result in injury to the spinal cord of the child, where an injury to the neck has occurred.

Figure 2B:
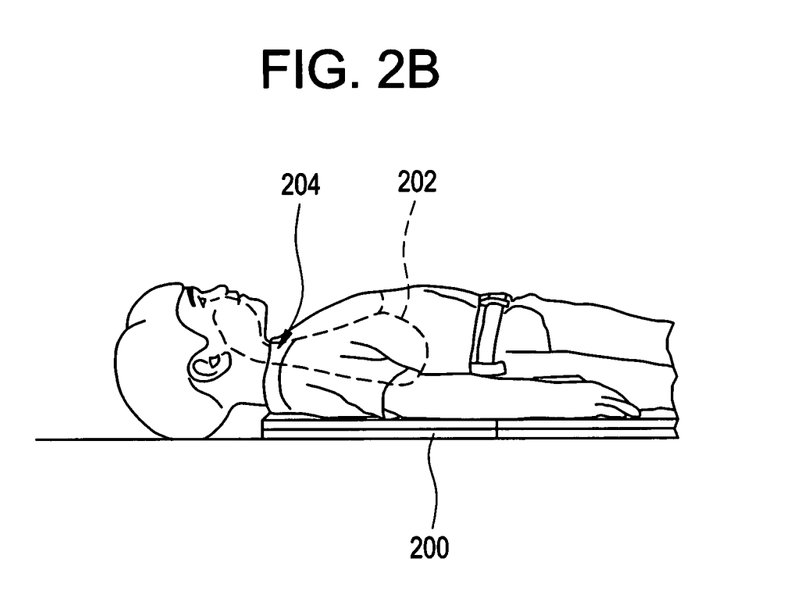
Figure 2C:
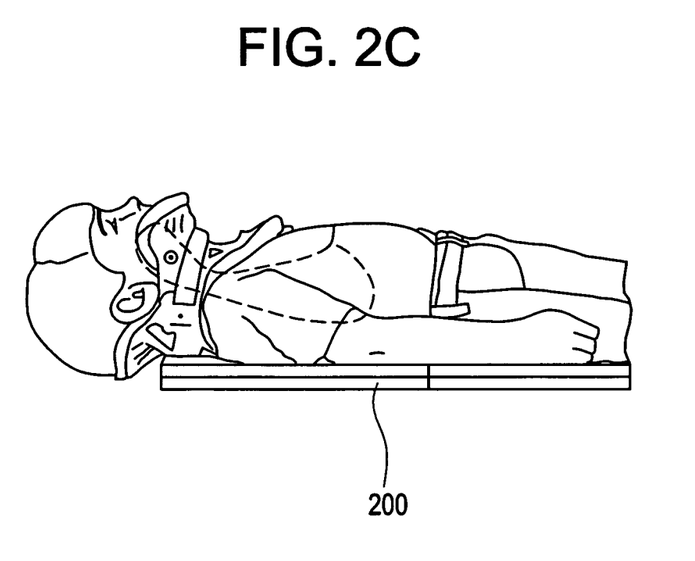

It has now been determined that by elevating the spine of a child, both the cervical spine and the airway can be aligned simultaneously to the benefit of the injured child. In this way, breathing is optimized without potential harm to the cervical spine or spinal cord of the child. FIGS. 2B-C and 3A show how, by placing a pad 200 or other lift beneath the spine of the child, appropriate alignment can be achieved. FIG. 3A shows that by elevating the spine, the extension of the child's occiput beyond the plane of the child's back, is accommodated for, thereby maintaining proper spinal alignment. It can be seen in FIG. 2B that airways, depicted by broken lines 202, are not restricted in section 204 when the child's spine is raised. In FIGS. 2B-C, the natural neutral alignment of the head and body of the child can be seen, and in both figures, the airway and cervical spine of the child are simultaneously aligned. Achievement of neutral alignment can be determined by checking to see that the external auditory meatus (the hole in the ear) is in line with the shoulder.

When elevating the spine of the child in order to achieve neutral alignment of both the airway and cervical spine, it is most desirable to elevate the entire spine of the child from the top border of the scapula to the base of the spine. As previously discussed, the proportionality of the child changes as the child develops. Therefore, the amount by which the child's spine must be raised in order to achieve neutral alignment depends upon the extent of maturity of the child. Physical maturity of a child can be measured in any one of several ways including age, weight, and length. While age is a convenient and reasonably reliable predictor of the physical maturity of the child, in the case of unconscious individuals, physical age can be difficult to ascertain. Likewise, in an emergency situation, it is difficult to visually gauge weight. Therefore the most convenient method by which to estimate the maturity of a child is height (or as the child is lying down, length). It may not be necessary to measure the entire child from head to toe in order to estimate maturity. Rather measuring certain portions of the child can yield a similarly reliable result. This can be a measurement from the shoulder or scapula to the base of the foot, from the knee to the hip, from the bottom of the foot to the top of the head or other appropriate measurements. This measurement can then be translated directly to the amount of elevation needed to place the cervical spine and airway in alignment. In a preferred embodiment of the invention, pad 200 has a measuring and translation system incorporated therein.

Figure 4A:
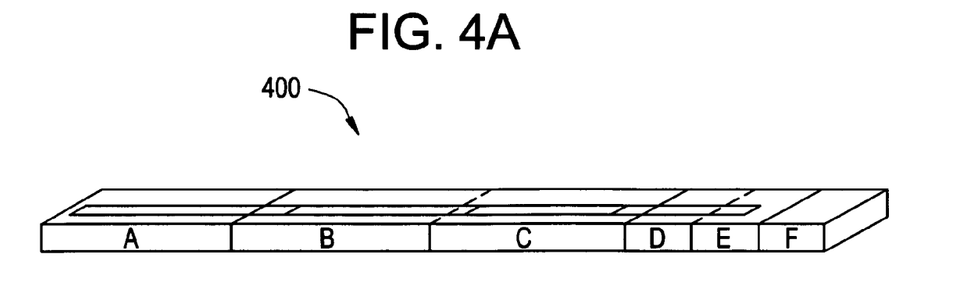
FIGS. 4A-E depict an airway pad according to an illustrative embodiment of the invention.
Figure 4B:
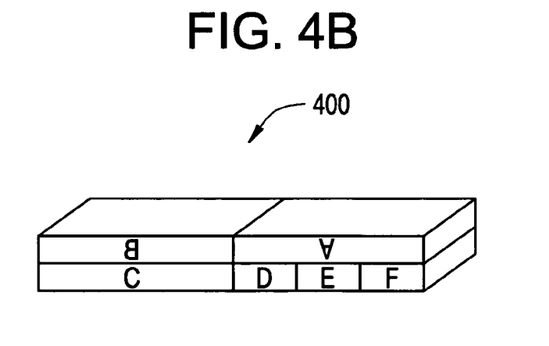
Figure 4C:
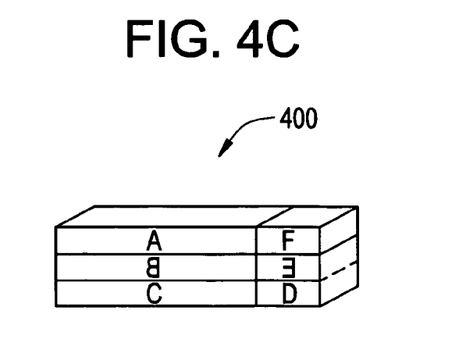
Figure 4D:
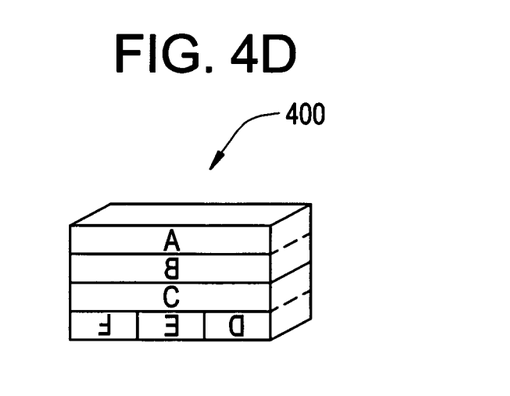
Figure 4E:
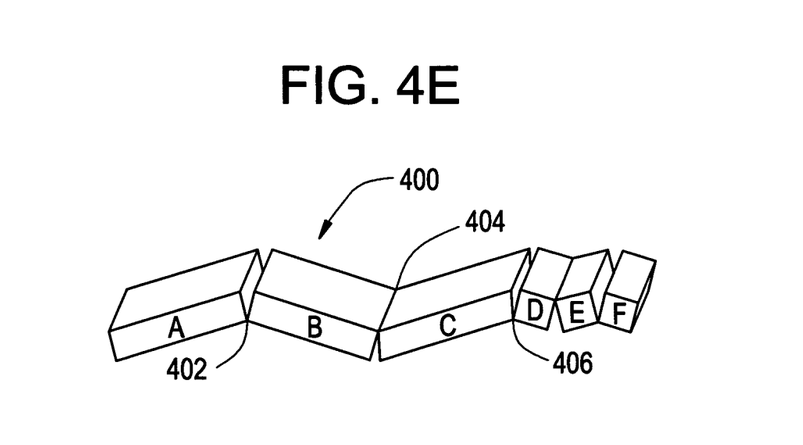

The invention includes a pad, referred to as an "airway pad" to raise a person's spine for optimum airway positioning. FIGS. 4A-E depict an airway pad 400 according to an illustration embodiment of the invention. Airway pad 400 comprises six separate but attached sections. These sections are labeled A through F. The labeling is for illustration purposes in the figures only, so that one may more easily understand how airway pad 400 is assembled and how it is folded to achieve different thicknesses of pad. The labeling also helps to show how holding the airway pad in different configurations results in a pad with a thickness of 1, 2, 3, or 4 thicknesses of pad. These are shown respectively in FIGS. 4A-D. The manner in which the different sections of the airway pad 400 are attached can be seen most easily from FIG. 4E. In this embodiment, adjacent pad sections are hinged either at a top surface or a bottom surface in an alternating fashion. FIG. 4E shows pad sections A and B hinged on a bottom surface at 402, pad sections B and C hinged on a top surface at 404, pad sections C and D hinged on a bottom surface at 406, and so on. Other patterns and locations of hinging are within the scope of the invention. Pad sections may also be secured on edge surfaces. Sections may be attached, for example, by hook and loop materials such as Velcro™, snaps or other fastening means. The line or points of attachment of separable pieces may function in a hinged manner.

Figure 5A:
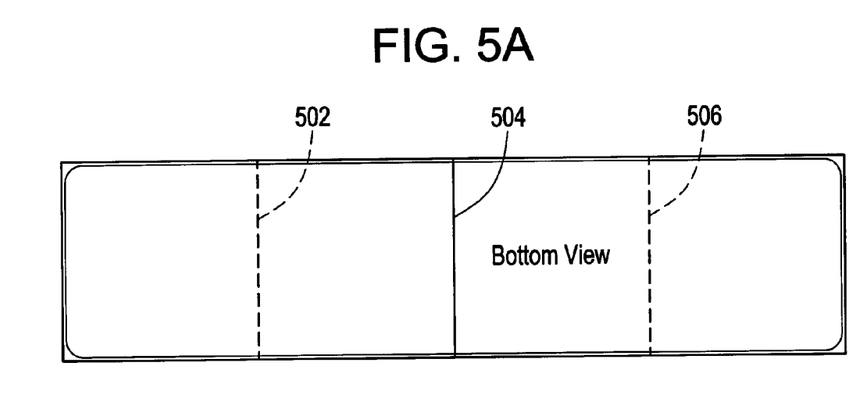
FIGS. 5A-B show a four-section airway pad according to an illustrative embodiment of the invention.
Figure 5B:
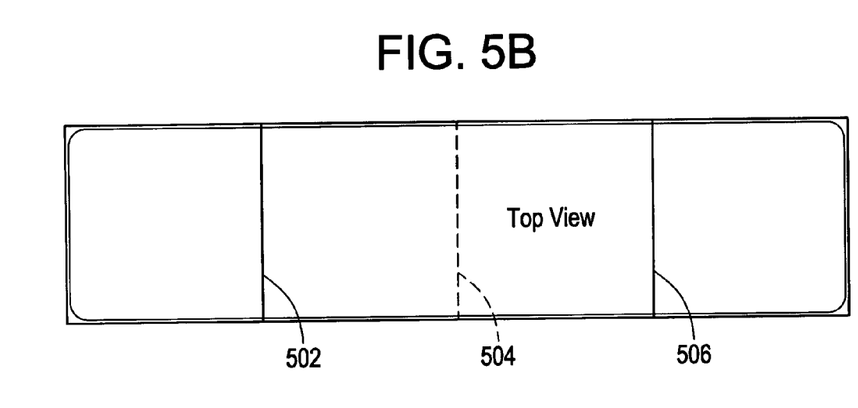

It is important to note that the airway pad 400 shown in FIGS. 4A-E is a preferred embodiment. It is not necessary that the pad be divided into sections precisely as shown in FIGS. 4A-E. Rather, the pad may be divided into any number of sections, and one or more of the sections may be separable from one another, instead of being attached as shown in FIGS. 4A-E. In a particular embodiment, the pad is divided into four sections, as shown in FIGS. 5A-B. In this embodiment, hinges 502, 504 and 506 alternate between the top and bottom of the pad moving along the pad. The sections of the pad may have differing thicknesses, so they can be used in different combinations to achieve the desired result.

In practice, prior to moving an injured child, the physical age of the child is estimated. This may be done by using a variety of methods. The following examples are intended to be non-limiting illustrations of estimating physical age. If the child is conscious, or someone who knows the child is available, the chronological age of the child can be ascertained and used to estimate the physical age. Alternatively, the child's weight or length (height) can be used to estimate physical age. Estimating weight generally requires moving the child. Where the child is injured and unconscious, this is undesirable. Thus, it is preferred, where the child is unconscious to estimate physical age by measuring the size of the child. This can be done, for instance, by checking the size of the extrication collar, which fits the child, or measuring the length of the child. To assist in measuring the length of the child, the airway pad can be equipped with a scale. The scale can be in inches or centimeters (or appropriate units of length) or it can have as few as 3 or 4 ranges, corresponding to thicknesses of airway pad needed.

The airway pad is unfolded and placed next to the child in order to measure the child and estimate the maturity of the child. The airway pad is then folded into the appropriate configuration and placed on a backboard or similar device. The child is then lifted and placed on the airway pad where the pad rests at or above the top of the shoulder of the child. It is most important, particularly for juveniles that the surface on which the head is positioned is lower than the surface on which the back rests. This is preferably accomplished by having the head extend fully over the edge of the airway pad as shown in FIG. 2B. As can be seen from FIGS. 2B-C, it is not important how far up the neck airway pad 200 extends. It may end just above the shoulders as shown in FIG. 2B or extend farther up the neck as shown in FIG. 2C.

Figure 6A:
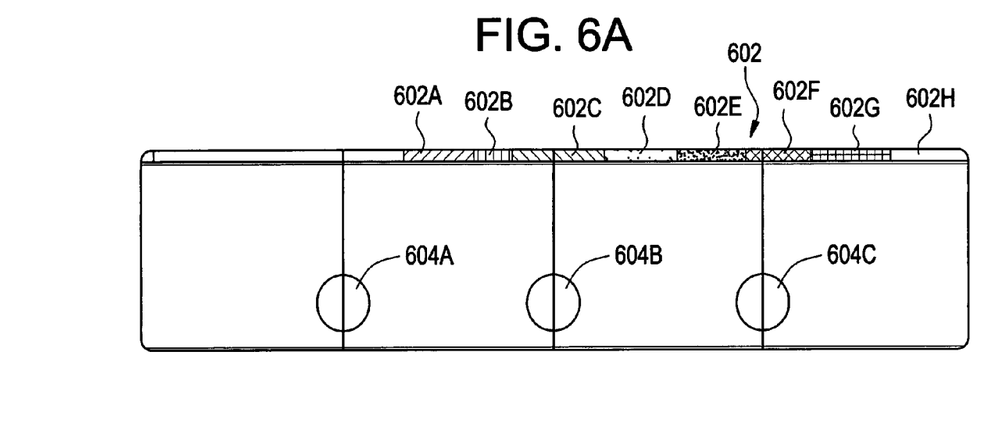
FIGS. 6A-B depict indicia on top and bottom surfaces of an airway pad according to an illustrative embodiment of the invention.
Figure 6B:
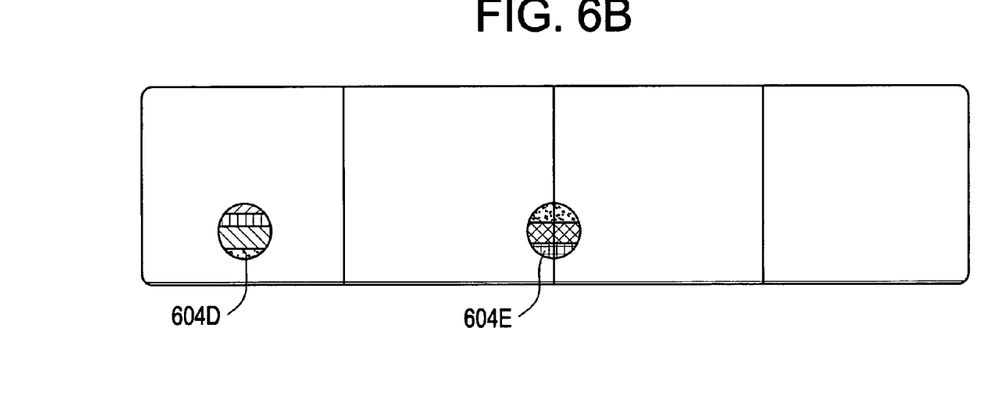
Figure 7A:
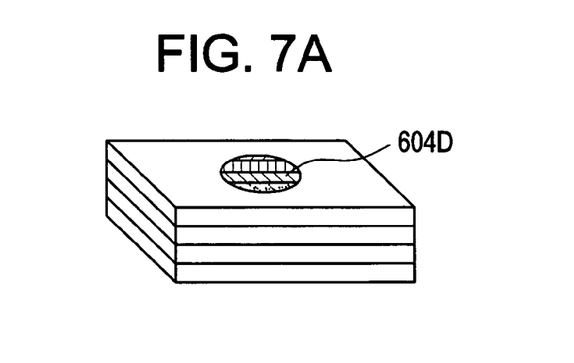
FIGS. 7A-C depict an airway pad folded to different thicknesses according to an illustrative embodiment of the invention.

Advantageously, the invention includes a way to easily fold the airway pad to a suitable thickness based on the size (height) of the patient. In general, the pad may include a measuring device for measuring the height of a person, wherein the measuring device corresponds to a mechanism for translating the height measurement into a pad elevation that will eliminate or reduce airway impairment. A preferred embodiment of such a mechanism is shown in FIGS. 6A-B. To facilitate measurement of a child and determination of the proper elevation for the spine of the child, indicia 602 and 604 can be placed upon airway pad 600 as shown in FIGS. 6A-B. FIG. 6A depicts one side of an unfolded airway pad, and FIG. 6B depicts the opposite side of the unfolded airway pad. Measuring indicia 602 provide a measuring device. In the embodiment shown in FIGS. 6A-B, the indicia include segments of different colors and widths. Indicia 602A-D represent a first height range, indicia 602E-G represent a second height range, and indicia 602H represents a third height range. A child can be measured against the indicia to determine in which height range the child is. Once the height range is determined, the pad is folded so that circular indicia 604, representing the colors and widths of the relevant height range, appear on top of the airway pad. This unique placement of indicia creates an easy way to configure the airway pad that can be used and understood by individuals regardless of their language or reading skills. For example, circular indicia 604D includes the colors and widths of the measuring indicia 602A-602D so that for a child of a height in the range represented by the measuring indicia 602A-D, the pad is folded so that the circular indicia 604D is visible, as shown in FIG. 7A.

Figure 7B:
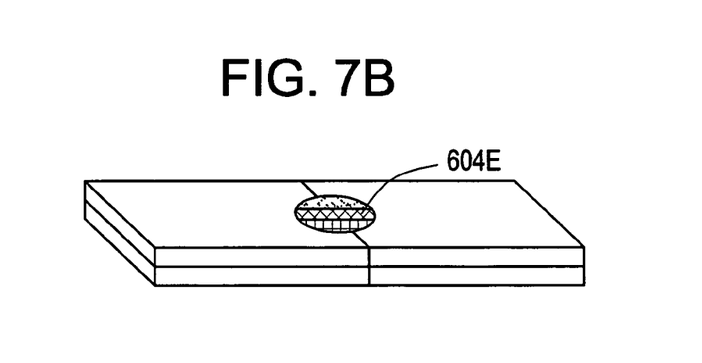

FIG. 7B shows a pad folded so that indicia 604E is visible. The colors and widths of indicia 604E correspond to that of the height range represented by indicia 602E-G. In this case the pad is folded so that it is two thicknesses in height.

Figure 7C:
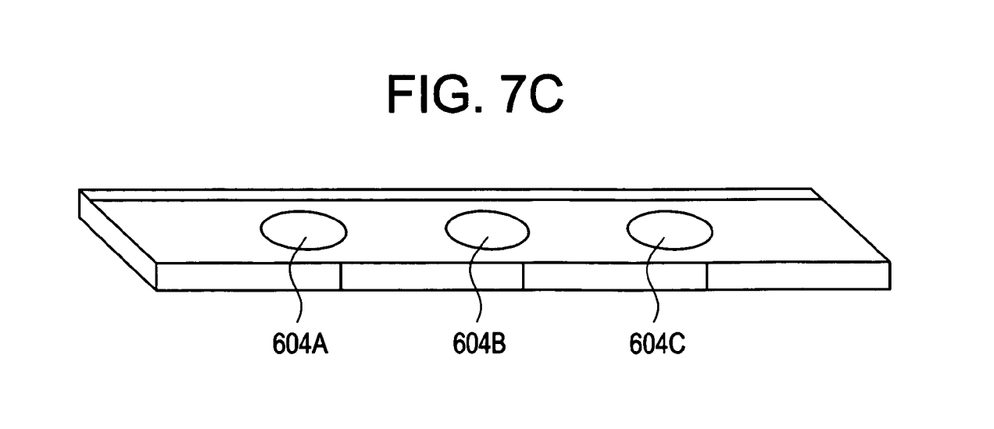

FIG. 7C shows an unfolded pad. In this form, indicia 604A-C are visible. Each is a solid color, which corresponds to the height range represented by the single indicia 602H.

Indicia need not be the specific widths and of varying colors as depicted in FIGS. 6A-B and 7A-C. For example, each height range can be represented by a single color. One or more bands of shapes could also be used for measurement, with a particular shape corresponding to a particular height range. Placement of the indicia may also vary from what is shown in FIGS. 6A-B and 7A-C. Indicia may also be placed on the edges of the pads.

In a broad sense, the invention includes a unique way to configure medical apparatus using indicia on, or coordinated with, the apparatus, although this idea has only been described here with respect to the airway pad.

As shown in FIGS. 2B-C, airway pad 200 of the present invention can be used with or without an extrication collar. By placing an airway pad on a planar surface such as a backboard, it in effect creates a two-tiered surface consisting of the plane, which is the top of the airway pad and a second, substantially parallel plane of the backboard. The child is then placed on the airway pad in a supine position with the head extending beyond the end of the airway pad, or to a lower level of the airway pad, as the case may be. The head of the child rests on the second, lower plane and the back of the child rests on the first, upper plane. It is not necessary that the child's entire body (other than the head) rest on the airway pad. It is most important that the pad extend to the lower end of the spine. The legs may rest off the pad without diminishing the effect of the pad on the alignment of the airway and cervical spine. Furthermore, the second, lower plane need not be a backboard. Any appropriate surface may serve to support the head, including the ground.

Figure 8:
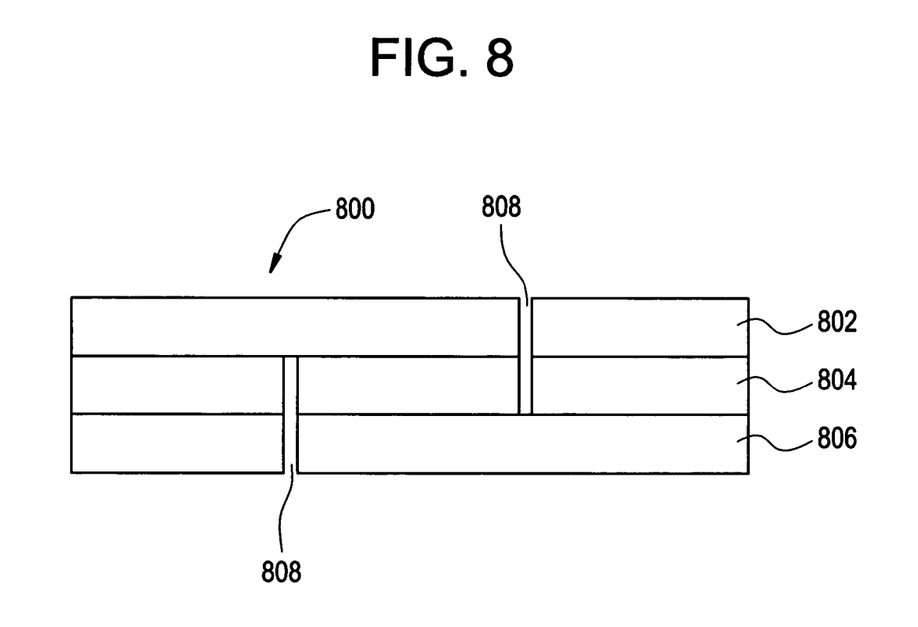
FIG. 8 is a magnified side view of an airway pad showing hinges according to an illustrative embodiment of the invention.

The airway pad of the present invention can be made from any suitable material. It can be as simple as pieces of wood or plywood, or it can be made from foam, either alone or covered with a suitable fabric or plastic covering. In one configuration, shown in FIG. 8, airway pad 800 is formed from three layers of foam 802, 804 and 806. Hinges 808 of airway pad 800 can be formed from the continuation of one layer of foam, or other material, and the cutting of the two remaining layers of foam, as can be seen in FIG. 8. As shown in FIG. 8, the three layers of foam constitute one layer of thickness of the pad. However by making cuts through two of the three layers, the remaining uncut layer forms a hinge, which allows the pad to be folded back upon itself. Since these pads are generally used in emergency situations, it is most desirable to have a pad, which is simply made and inexpensive so that it may be disposed of once used. Further, in certain trauma situations blood is present, and once the pad comes in contact with blood, for hygienic reasons, it should be disposed of. Therefore, a cost effective and disposable pad is most desirable. Using three layers of joined foam makes this configuration inexpensive and therefore more readily disposable than a cloth covered airway pad.

However, cloth covered airway pads are contemplated by this invention for use in one other area. That is that parents are now encouraged to lay infants in a supine position while the infant is sleeping. This may compromise the airway of the infant. Therefore, the airway pad of the present invention finds use in allowing the infant to sleep more comfortably by allowing alignment of the airway and cervical spine while the infant lies on its back in a crib. This allows the infant to be more comfortable and breathe more easily, and may contribute to reduced incidents of sudden infant death syndrome (SIDS), if such is linked to constriction of the airway of the infant during resting in a supine position.

The present invention has been described with reference to its preferred embodiments. Although the invention is described primarily as it relates to children, there can be instances wherein the invention can be applied to older individuals. Various details and applications of the invention may be changed without departing from its spirit and scope. For example, modifications to the indicia, pad configurations and uses of the pad or other apparatus can be made within the spirit and scope of the invention. Furthermore, the foregoing description of the preferred embodiment of an airway pad according to the present invention is provided for the purpose of illustration only and not for the purpose of limitation.

The invention claimed is:

1. A pad for aligning the airways and spine of a child, the pad comprising:
   a plurality of sections joined together such that the pad can be configured to a plurality of thicknesses by folding or unfolding the pad, and wherein a particular configuration of the pad is suitable to simultaneously align the spine and airways of a child;
   a measuring device having indicia to represent a measurement of a child so that when a child is measured with the measuring device, particular indicia is(are) identified as corresponding to the measurement;
   indicia on the pad corresponding to the indicia on the measuring device,
   wherein the pad can be configured so that only the indicia corresponding to the particular indicia identified as corresponding to the measurement are visible, and when the pad is so configured, positioning the measured child on the pad will cause the child's airways and spine to be simultaneously aligned.

2. The pad of claim 1 comprising four sections that can be adjusted to thickness of 1, 2, 3 or 4 sections.

3. The pad of claim 1 comprising six sections that can be adjusted to a thickness of at least 1, 2, 3 or 4 sections.

4. The pad of claim 1 wherein the measuring device is for measuring the length of a child or a portion thereof.

5. The pad of claim 1 wherein the pad comprises two sets of three identical sections each.

6. The pad of claim 5 wherein one set of sections is one third of the size of the other set of sections.

7. The pad of claim 1 wherein two or more of the plurality of sections are permanently joined.

8. The pad of claim 1 wherein two or more of the plurality of sections are detachably joined.

* * * * *